United States Patent
Sugiyama et al.

(10) Patent No.: US 11,340,165 B2
(45) Date of Patent: May 24, 2022

(54) SAMPLE OBSERVATION DEVICE AND SAMPLE OBSERVATION METHOD

(71) Applicant: HAMAMATSU PHOTONICS K.K., Hamamatsu (JP)

(72) Inventors: Norikazu Sugiyama, Hamamatsu (JP); Masanori Matsubara, Hamamatsu (JP); Satoshi Yamamoto, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 193 days.

(21) Appl. No.: 16/629,326

(22) PCT Filed: Apr. 10, 2018

(86) PCT No.: PCT/JP2018/015093
§ 371 (c)(1),
(2) Date: Jan. 8, 2020

(87) PCT Pub. No.: WO2019/012765
PCT Pub. Date: Jan. 17, 2019

(65) Prior Publication Data
US 2021/0116373 A1    Apr. 22, 2021

(30) Foreign Application Priority Data

Jul. 11, 2017 (JP) .............................. JP2017-135427

(51) Int. Cl.
*G01N 21/64* (2006.01)
*C12Q 1/06* (2006.01)
(Continued)

(52) U.S. Cl.
CPC .......... *G01N 21/6428* (2013.01); *C12Q 1/06* (2013.01); *G01N 1/30* (2013.01); *G01N 1/312* (2013.01);
(Continued)

(58) Field of Classification Search
CPC . C12Q 1/06; G01N 1/30; G01N 1/312; G01N 15/1463; G01N 2001/1006;
(Continued)

(56) References Cited

U.S. PATENT DOCUMENTS

| | | |
|---|---|---|
| 8,582,203 B2 | 11/2013 | Dunsby |
| 2004/0197771 A1 | 10/2004 | Powers et al. |

(Continued)

FOREIGN PATENT DOCUMENTS

| | | |
|---|---|---|
| CN | 1681937 A | 10/2005 |
| JP | 2005-292112 A | 10/2005 |

(Continued)

OTHER PUBLICATIONS

Molteni Raffaella et al., "A novel device to concurrently assess leukocyte extravasation and interstitial migration within a defined 3D environment", Lab on a Chip, Jan. 1, 2015, vol. 15, p. 195-p. 207, XP55774122.

(Continued)

*Primary Examiner* — Mark R Gaworecki
(74) *Attorney, Agent, or Firm* — Faegre Drinker Biddle & Reath LLP

(57) ABSTRACT

A sample observation device includes an imaging unit that images observation light generated due to irradiation with the planar light that is transmitted through a membrane filter and outputs fluorescent light image data, a partial image generation unit that specifies a first area corresponding to a first sample holding space and a second area corresponding to a second sample holding space in the fluorescent light image data, and generates first partial image data corresponding to the first area and second partial image data corresponding to the second area, an observation image generation unit that generates first observation image data and second observation image data on the basis of the partial (Continued)

image data, and an analysis unit that analyzes a sample on the basis of the first observation image data and the second observation image data.

14 Claims, 12 Drawing Sheets

(51) Int. Cl.
*G01N 1/30* (2006.01)
*G01N 1/06* (2006.01)
*G01N 21/51* (2006.01)
*G06T 7/00* (2017.01)
*G01N 15/14* (2006.01)
*G01N 21/00* (2006.01)
*G01N 1/31* (2006.01)
*G02B 21/00* (2006.01)
*G02B 21/18* (2006.01)
*G02B 21/26* (2006.01)
*G02B 21/36* (2006.01)
*G01N 21/17* (2006.01)
*G01N 15/10* (2006.01)

(52) U.S. Cl.
CPC ......... *G01N 15/1463* (2013.01); *G01N 21/51* (2013.01); *G01N 21/6458* (2013.01); *G02B 21/0032* (2013.01); *G02B 21/0076* (2013.01); *G02B 21/18* (2013.01); *G02B 21/26* (2013.01); *G02B 21/367* (2013.01); *G06T 7/0012* (2013.01); *G01N 21/6452* (2013.01); *G01N 2001/302* (2013.01); *G01N 2015/1006* (2013.01); *G01N 2021/1738* (2013.01); *G01N 2021/6419* (2013.01); *G01N 2021/6439* (2013.01); *G01N 2021/6441* (2013.01); *G01N 2021/6471* (2013.01); *G01N 2021/6482* (2013.01); *G06T 2207/10064* (2013.01); *G06T 2207/30024* (2013.01); *G06T 2207/30072* (2013.01); *G06T 2207/30242* (2013.01)

(58) Field of Classification Search
CPC ..... G01N 2001/302; G01N 2015/1006; G01N 2021/1738; G01N 2021/6419; G01N 2021/6439; G01N 2021/6441; G01N 2021/6471; G01N 21/51; G01N 21/6428; G01N 21/6452; G01N 21/6458; G02B 21/0032; G02B 21/0076; G02B 21/18; G02B 21/26; G02B 21/367; G06T 2207/10064; G06T 2207/30024; G06T 2207/30072; G06T 2207/30242; G06T 7/0012

See application file for complete search history.

(56) References Cited

U.S. PATENT DOCUMENTS

| 2008/0032324 A1* | 2/2008 | Walt .................. G01N 21/6458 435/29 |
| 2012/0315660 A1 | 12/2012 | Schroeder et al. |
| 2014/0127744 A1 | 5/2014 | Schroeder et al. |
| 2016/0139394 A1 | 5/2016 | Taniguichi et al. |

FOREIGN PATENT DOCUMENTS

| JP | 2006-220954 A | 8/2006 |
| JP | 2006-280296 A | 10/2006 |
| JP | 2016-522880 A | 8/2016 |
| WO | WO-2014/141034 A2 | 9/2014 |

OTHER PUBLICATIONS

International Preliminary Report on Patentability dated Jan. 23, 2020 for PCT/JP2018/015093.
Hulkower I., Keren et al., "Cell Migration and Invasion Assays as Tools for Drug Discovery," Pharmaceutics, 2011, Mar, pp. 107-124.
Kramer, Nina et al., "In vitro cell migration and invasion assays," Mutation Research, 752 (2013), pp. 10-24.
Mastyugin, Vladimir et al., "A Quantitative High-Throughput Endothelial Cell Migration Assay," Journal of Biomolecular Screening 9(8), Dec. 1, 2004, pp. 712-718.
Tovari, Jozsef et al., "Boyden chamber-based method for characterizing the distribution of adhesions and cytoskeletal structure in HT1080 fibrosarcoma cells," Cell Adhesion & Migration, Oct. 31, 2014, vol. 8, pp. 509-516.
Mei Jie et al., "Study on effect of peptide-conjugated near-infrared fluorescent quantum dots on invasion and metastasis of human buccal squamous cell carcinoma cell line BcaCD885", West China Journal of Stomatology, 2011, vol. 29 No, 1, p. 92-p. 95, (with English Language Abstract).

* cited by examiner (a)

(b)

SAMPLE OBSERVATION DEVICE AND SAMPLE OBSERVATION METHOD

TECHNICAL FIELD

The present disclosure relates to a sample observation device and a sample observation method.

BACKGROUND ART

In the related art, a scheme for evaluating the mobility of a sample such as a cancer cell using a membrane filter is known (see, for example, Non-Patent Literature 1 to 3). An example of the evaluation of the mobility includes invasive ability evaluation (Cell Invasion Assay). Invasion ability evaluation is mainly to evaluate the ability of cancer cells to migrate while destroying an extracellular matrix. In the invasive ability evaluation, the ability of cells to pass through a membrane filter coated with an extracellular matrix is evaluated.

Cancer cells have properties of migration to more nutritious areas. Therefore, in a sample container, one of two spaces partitioned by a membrane filter is filled with an undernourished solution and the other is filled with a nutritious solution, such that cells can migrate from the one space to the other space through micropores of the membrane filter.

PRIOR ART LITERATURE

Non-Patent Literature

[Non-Patent Literature 1] Nina Kramer et al., "In vitro cell migration and invasion assays" Mutation Research 752 (2013) 10-24

[Non-Patent Literature 2] Keren I. Hulkower and Renee L. Herber "Cell Migration and Invasion Assays as Tools for Drug Discovery" Pharmaceutics 2011, 3, 107-124; doi: 10.3390/pharmaceutics3010107

[Non-Patent Literature 3] Vladimir Mastyugin et al., "A Quantitative High-Throughput Endothelial Cell Migration Assay" Journal of Biomolecular Screening 9 (8); 2004

SUMMARY OF INVENTION

Technical Problem

In the related art, a sample that has moved from one space to the other space through a membrane filter has been labeled with fluorescence and observed with a plate reader, and comparison with a control (a state of being not treated with a drug) has been performed. However, in such a scheme of the related art, it is difficult to observe both the sample that has moved from the one space to the other space through the membrane filter and a sample that has not moved.

With only observing the sample that has moved through the membrane filter, it is difficult to distinguish a phenomenon such as cell proliferation or cell death from the invasion ability of the cell according to a case in which an observation time becomes longer or an action of a drug. Therefore, it is conceivable that the accuracy of evaluation of invasion ability cannot be sufficiently secured. In order to improve the accuracy of the evaluation of the invasion ability, it is preferable to obtain the viability of each of the sample that has moved through the membrane filter and the sample that has not moved.

The present disclosure has been made to solve the above-described problems, and an object thereof is to provide a sample observation device and a sample observation method capable of observing both a sample that has moved through a membrane filter and a sample that has not moved.

Solution to Problem

A sample observation device according to an aspect of the present disclosure is a sample observation device for observing a sample held in a sample container having a first sample holding space and a second sample holding space partitioned by a membrane filter, the sample observation device including: an irradiation optical system that irradiates the sample with planar light including a wavelength that is transmitted through the membrane filter as excitation light; a scanning unit that scans the sample with respect to an irradiation surface for the planar light; an imaging unit that images observation light including fluorescent light generated due to the irradiation with the planar light and outputs fluorescent light image data based on an imaging result; a partial image generation unit that specifies a first area corresponding to the first sample holding space and a second area corresponding to the second sample holding space in the fluorescent light image data, and generates first partial image data corresponding to the first area and second partial image data corresponding to the second area; an observation image generation unit that generates first observation image data on the basis of the first partial image data and generates second observation image data on the basis of the second partial image data; and an analysis unit that analyzes the sample on the basis of the first observation image data and the second observation image data.

In the sample observation device, the sample is irradiated with the planar light including the wavelength that is transmitted through the membrane filter as excitation light. Accordingly, the fluorescent light image data based on the imaging result of the observation light including the fluorescent light from both the first sample holding space and the second sample holding space partitioned by the membrane filter can be acquired. Further, in the sample observation device, the first area corresponding to the first sample holding space and the second area corresponding to the second sample holding space are specified from the acquired fluorescent light image data, and the observation image data based on the partial image data of each area is generated. Accordingly, both the sample that has moved through the membrane filter and the sample that has not moved can be observed.

Further, the imaging unit may further image scattered light of the excitation light generated due to the irradiation with the planar light, and output scattered light image data based on an imaging result, and the partial image generation unit may specify the first area and the second area in the fluorescent light image data on the basis of the scattered light image data. In this case, the area corresponding to the membrane filter in the fluorescent light image data can be specified using the scattered light image data. Therefore, the first area and the second area in the fluorescent light image data can be easily specified.

Further, the irradiation optical system may irradiate the sample with first planar light including a wavelength that is transmitted through the membrane filter and second planar light including a wavelength that is not transmitted through the membrane filter as the excitation light, the imaging unit may image observation light including first fluorescent light generated due to irradiation with the first planar light and observation light including second fluorescent light generated due to irradiation with the second planar light, and output first fluorescent light image data and second fluorescent light image data based on respective imaging results, and the partial image generation unit may specify the first area and the second area in the first fluorescent light image data on the basis of the second fluorescent light image data. In this case, fluorescent light images from both the sample holding spaces with the membrane filter sandwiched therebetween is included in the first fluorescent light image data, whereas only the fluorescent light image from one of the sample holding spaces with the membrane filter sandwiched therebetween is included in the second fluorescent light image data. Therefore, the first area and the second area in the first fluorescent light image data can be easily specified through collation of the first fluorescent light image data and the second fluorescent light image data.

Further, the sample may be stained with a first fluorescent substance excited by light having a wavelength that is transmitted through the membrane filter, and a second fluorescent substance excited by light having a wavelength that is not transmitted through the membrane filter. In this case, the area corresponding to the first sample holding space and the area corresponding to the second sample holding space can be easily discriminated on the basis of the fluorescent light image of the sample included in the first fluorescent light image data and the fluorescent light image of the sample included in the second fluorescent light image data. Therefore, the first area and the second area in the first fluorescent light image data can be easily specified through collation of the first fluorescent light image data and the second fluorescent light image data.

Further, the sample may be stained with a first fluorescent substance excited by light having a wavelength that is transmitted through the membrane filter, and a solution including a second fluorescent substance excited by light having a wavelength that is not transmitted through the membrane filter may be injected into the first sample holding space and the second sample holding space. In this case, the area corresponding to the first sample holding space and the area corresponding to the second sample holding space can be easily discriminated on the basis of a fluorescent light image of a solution. Therefore, the first area and the second area in the first fluorescent light image data can be easily specified through collation of the first fluorescent light image data and the second fluorescent light image data.

Further, the analysis unit may count the number of samples located in the first sample holding space and the number of samples located in the second sample holding space on the basis of the first observation image data and the second observation image data. Accordingly, evaluation of the samples can be performed rapidly.

Further, the sample observation device may further include an image formation optical system that has an observation axis inclined with respect to the irradiation surface and that forms an image of the observation light on the imaging unit. In this case, a field-of-view selection operation becomes unnecessary, and scanning and imaging of the sample can be performed simultaneously. Therefore, improvement of a throughput until the observation image data is obtained can be achieved.

A sample observation method according to an aspect of the present disclosure is a sample observation method for observing a sample held in a sample container having a first sample holding space and a second sample holding space partitioned by a membrane filter, the sample observation method including: an irradiation step of irradiating the sample with planar light including a wavelength that is transmitted through the membrane filter as excitation light; a scanning step of scanning the sample with respect to an irradiation surface for the planar light; an imaging step of imaging observation light including fluorescent light generated due to the irradiation with the planar light and outputting fluorescent light image data based on an imaging result; a partial image generation step of specifying a first area corresponding to the first sample holding space and a second area corresponding to the second sample holding space in the fluorescent light image data, and generating first partial image data corresponding to the first area and second partial image data corresponding to the second area; an observation image generation step of generating first observation image data on the basis of the first partial image data and generating second observation image data on the basis of the second partial image data; and an analysis step of analyzing the sample on the basis of the first observation image data and the second observation image data.

In the sample observation method, the sample is irradiated with the planar light including the wavelength that is transmitted through the membrane filter as excitation light. Accordingly, the fluorescent light image data based on the imaging result of the observation light including the fluorescent light from both the first sample holding space and the second sample holding space partitioned by the membrane filter can be acquired. Further, in the sample observation method, the first area corresponding to the first sample holding space and the second area corresponding to the second sample holding space are specified from the acquired fluorescent light image data, and the observation image data based on the partial image data of each area is generated. Accordingly, both the sample that has moved through the membrane filter and the sample that has not moved can be observed.

Further, the imaging step may include further imaging scattered light of the excitation light generated due to the irradiation with the planar light, and outputting scattered light image data based on an imaging result, and the partial image generation step may include specifying the first area and the second area in the fluorescent light image data on the basis of the scattered light image data. In this case, the area corresponding to the membrane filter in the fluorescent light image data can be specified using the scattered light image data. Therefore, the first area and the second area in the fluorescent light image data can be easily specified.

Further, the irradiation step may include irradiating the sample with first planar light including a wavelength that is transmitted through the membrane filter and second planar light including a wavelength that is not transmitted through the membrane filter as the excitation light, the imaging step may include imaging observation light including first fluorescent light generated due to irradiation with the first planar light and observation light including second fluorescent light generated due to irradiation with the second planar light, and outputting first fluorescent light image data and second fluorescent light image data based on respective imaging results, and the partial image generation step may include specifying the first area and the second area in the first fluorescent light image data on the basis of the second fluorescent light image data. In this case, fluorescent light images from both the sample holding spaces with the membrane filter sandwiched therebetween is included in the first fluorescent light image data, whereas only the fluorescent light image from one of the sample holding spaces with the membrane filter sandwiched therebetween is included in the second fluorescent light image data. Therefore, the first area and the second area in the first fluorescent light image data can be easily specified through collation of the first fluorescent light image data and the second fluorescent light image data.

Further, the sample observation method may further include a preparation step of staining the sample with a first fluorescent substance excited by light having a wavelength that is transmitted through the membrane filter, and a second fluorescent substance excited by light having a wavelength that is not transmitted through the membrane filter. In this case, the area corresponding to the first sample holding space and the area corresponding to the second sample holding space can be easily discriminated on the basis of the fluorescent light image of the sample included in the first fluorescent light image data and the fluorescent light image of the sample included in the second fluorescent light image data. Therefore, the first area and the second area in the first fluorescent light image data can be easily specified through collation of the first fluorescent light image data and the second fluorescent light image data.

Further, the sample observation method may further include a preparation step of staining the sample with a first fluorescent substance excited by light having a wavelength that is transmitted through the membrane filter, and injecting a solution including a second fluorescent substance excited by light having a wavelength that is not transmitted through the membrane filter into the first sample holding space and the second sample holding space. In this case, the area corresponding to the first sample holding space and the area corresponding to the second sample holding space can be easily discriminated on the basis of a fluorescent light image of a solution. Therefore, the first area and the second area in the first fluorescent light image data can be easily specified through collation of the first fluorescent light image data and the second fluorescent light image data.

Further, the analysis step may include counting the number of samples located in the first sample holding space and the number of samples located in the second sample holding space on the basis of the first observation image data and the second observation image data. Accordingly, evaluation of the samples can be performed rapidly.

Further, the imaging step may include forming an image of the observation light according to an observation axis inclined with respect to the irradiation surface. In this case, a field-of-view selection operation becomes unnecessary, and scanning and imaging of the sample can be performed simultaneously. Therefore, improvement of a throughput until the observation image data is obtained can be achieved.

Advantageous Effects of Invention

In the sample observation device and the sample observation method, both the sample that has moved through the membrane filter and the sample that has not moved can be observed.

BRIEF DESCRIPTION OF DRAWINGS

FIG. 8 is a flowchart illustrating an example of a sample observation method using the sample observation device illustrated in

FIG. 1.

DESCRIPTION OF EMBODIMENTS

Hereinafter, preferred embodiments of a sample observation device and a sample observation method according to an aspect of the present invention will be described in detail with reference to the drawings.

Figure 1:
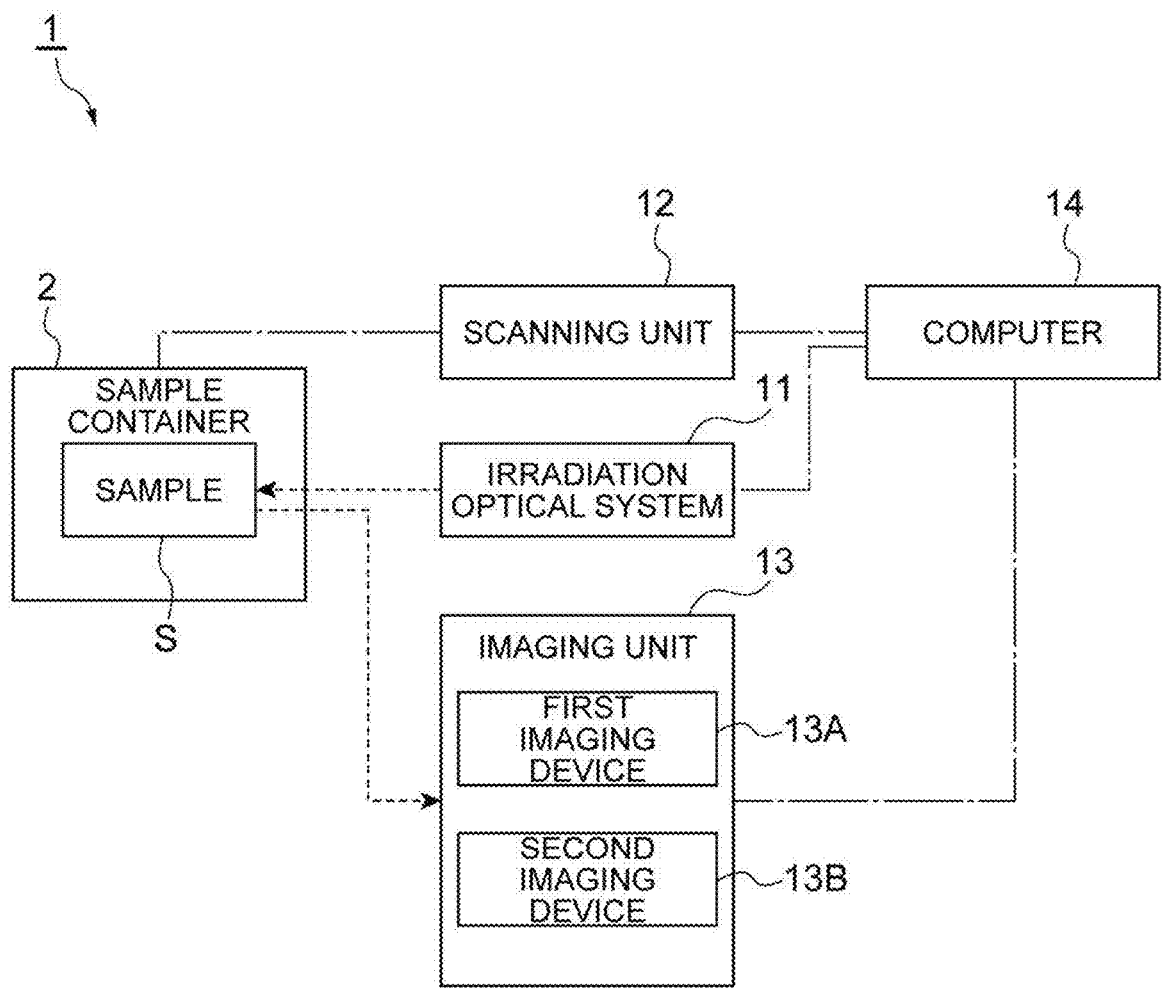
FIG. 1 is a block diagram illustrating an embodiment of a sample observation device.

FIG. 1 is a block diagram illustrating an embodiment of a sample observation device. This sample observation device 1 is a device that causes fluorescent light and/or scattered light generated inside a sample S to be formed as an image on an image formation surface to acquire observation image data of the sample S, and analyzes and evaluates the sample S on the basis of the observation image data.

An example of this type of sample observation device 1 includes a slide scanner that acquires and displays an image of the sample S held on a slide glass, or a plate reader that acquires image data of the sample S held on a microplate and analyzes the image data. Examples of the sample S that is an observation target include a cell and tissue of a human or an animal. The sample S is stained with a fluorescent substance excited by planar light L2 to be described. Examples of the fluorescent substance include calcein AM (excitation wavelength 490 nm/fluorescent light wavelength 525 nm), calcein blue (excitation wavelength 360 nm/fluorescent light wavelength 450 nm). When these fluorescent substances are used, living cells can be selectively stained.

Figure 2:
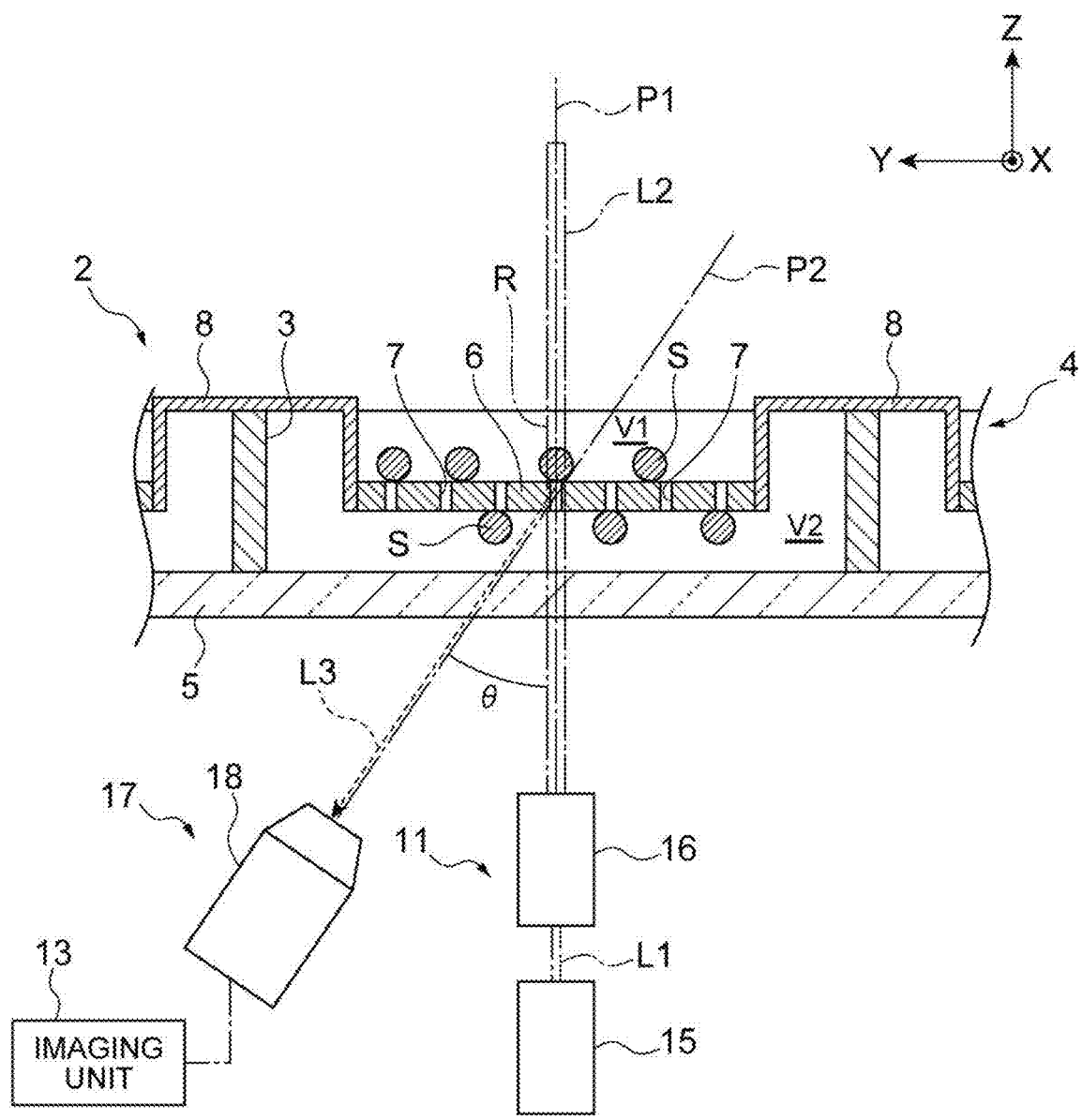
FIG. 2 is a schematic diagram illustrating a configuration example of an irradiation optical system, a sample container, and an image formation optical system in the sample observation device illustrated in FIG. 1.

The sample S is held in a sample container 2 as illustrated in FIG. 2. The sample container 2 is, for example, a microplate. The sample container 2 includes a plate-like main body 4 in which a plurality of wells 3 in which the samples S are disposed are arranged in a straight line (or a matrix form), and a plate-like transparent member 5 provided to close one end side of the well 3 on one surface side of the main body 4.

A membrane filter 6 is disposed in the well 3. The membrane filter 6 is a film in which a large number of micropores 7 through which the sample S passes are provided. A material of the membrane filter 6 is, for example, polycarbonate or polyethylene terephthalate. A thickness of the membrane filter 6 is generally very thin and is, for example, about 7 µm to 25 µm. Further, an inner diameter (a diameter) of the micropores 7 is, for example, about 8 µm to 10 µm. The membrane filter 6 is held at a substantially center position of the well 3 by a support member 8 to partition the well 3 into a first sample holding space V1 on the opposite side to the transparent member 5 and a second sample holding space V2 on the transparent member 5 side.

When the samples S that are observation targets are cancer cells, the samples S are held on one surface of the membrane filter 6 coated with the extracellular matrix so that the samples S are located on the first sample holding space V1 side. Some of the samples S held on the one surface of the membrane filter 6 enter the micropores 7 of the membrane filter 6 over time, and move to the other surface of the membrane filter 6 (that is, the second sample holding space V2) through the micropores 7. Therefore, invasion ability of the cancer cells can be evaluated by observing the sample S present on the one surface of the membrane filter 6 and the sample S present on the other surface of the membrane filter 6 after a predetermined time has elapsed since the sample S came to be held on the one surface of the membrane filter 6.

As illustrated in FIG. 1, the sample observation device 1 includes an irradiation optical system 11, a scanning unit 12, an imaging unit 13, and a computer 14. The irradiation optical system 11 irradiates the sample S with the planar light L2 including a wavelength that is transmitted through the membrane filter 6 as excitation light. The irradiation optical system 11 includes a light source 15 and a planar light formation unit 16, as illustrated in FIG. 2. The light source 15 outputs light L1 that is a formation source of the planar light L2. Examples of the light source 15 include a laser light source such as a laser diode and a solid-state laser light source. Further, the light source 15 may be a light emitting diode, a super luminescent diode, or a lamp light source. The light L1 output from the light source 15 is guided to the planar light formation unit 16.

The planar light formation unit 16 shapes the light L1 output from the light source 15 into the planar light L2, and irradiates the sample S with the shaped planar light L2 along the optical axis P1. In the embodiment, an optical axis of the planar light formation unit 16 is the optical axis P1 of the planar light L2. The planar light formation unit 16 includes a light shaping element such as a cylindrical lens, an axicon lens, or a spatial light modulator, and is optically coupled to the light source 15. The planar light formation unit 16 may include an objective lens, an optical shutter, and the like.

When the membrane filter 6 is made of polycarbonate, the membrane filter 6 is impermeable to light having a wavelength of 400 nm or less. Therefore, it is preferable for the wavelengths of the light L1 and the planar light L2 to be, for example, 450 nm to 750 nm. When observation is performed in a thickness direction of the sample S, it is preferable for the planar light L2 to be thin planar light having a thickness of 2 mm or less in consideration of resolution. Further, when a thickness of the sample S is very small, that is, when a sample S having a thickness equal to or less than Z-direction resolution is observed, a thickness of the planar light L2 does not affect the resolution. In this case, planar light L2 having a thickness exceeding 2 mm may be used.

The sample S held in the sample container 2 is irradiated with the planar light L2 formed by the irradiation optical system 11. As described above, the planar light L2 includes a wavelength that is transmitted through the membrane filter 6. Therefore, the irradiation surface R for the planar light L2 with respect to the sample S reaches the second sample holding space V2 through the membrane filter 6 from the first sample holding space V1. Due to the irradiation with the planar light L2, the observation light L3 is generated on the irradiation surface R for the planar light L2. The observation light L3 includes, for example, fluorescent light excited in the sample S due to the planar light L2 and scattered light of the planar light L2 scattered on the surface of the membrane filter 6 without passing through the membrane filter 6.

The scanning unit 12 is a mechanism that scans the sample S with respect to the irradiation surface R for the planar light L2. The scanning unit 12 includes a moving stage that moves the sample container 2 that holds the samples S, for example. The moving stage scans the sample container 2 in a preset direction according to a control signal from the computer 14. In the embodiment, the moving stage scans the sample container 2 in one direction within a plane orthogonal to the optical axis P1 of the planar light L2. In the following description, a direction of the optical axis P1 of the planar light L2 is referred to as an Z axis, a scanning direction of the sample container 2 according to the moving stage is referred to as a Y axis, and a direction orthogonal to the Y axis within the plane orthogonal to the optical axis P1 of the planar light L2 is referred to as an X axis, as illustrated in FIG. 2. The irradiation surface R for the planar light L2 with respect to the sample S is a surface within the XZ plane.

In the embodiment, as illustrated in FIG. 2, an image formation optical system 17 that forms an image of the observation light L3 generated on the irradiation surface R due to the irradiation with the planar light L2 is provided. As illustrated in FIG. 2, the image formation optical system 17 includes, for example, an objective lens 18. The image formation optical system 17 may include an image formation lens, in addition to the objective lens 18. An optical axis of the image formation optical system 17 is an observation axis P2 of the observation light L3. This observation axis P2 is inclined at an inclination angle θ with respect to the irradiation surface R for the planar light L2. The inclination angle θ also matches an angle formed by the optical axis P1 of the planar light L2 directed to the sample S and the observation axis P2. The inclination angle θ is 10° to 80°. The inclination angle θ is preferably 20° to 70° from the viewpoint of improvement of resolution of the observation image. Further, the inclination angle θ is more preferably 30° to 65° from the viewpoint of improvement of the resolution of the observation image and stability of the field of view.

As illustrated in FIG. 1, the imaging unit 13 is configured of an imaging device that images the observation light L3 and outputs fluorescent light image data based on an imaging result. In the embodiment, the imaging unit 13 includes a first imaging device (a first photodetector) 13A that images fluorescent light generated due to the irradiation with the planar light L2 and a second imaging device (a second photodetector) 13B that images the scattered light of the planar light L2 generated on the surface of the membrane filter 6.

Examples of the first imaging device 13A and the second imaging device 13B include area image sensors such as CMOS image sensors and CCD image sensors. These area image sensors are disposed on an image formation surface according to the image formation optical system 17, image a light image using, for example, a global shutter or a rolling shutter, and output two-dimensional image data to the computer 14. A filter that cuts scattered light may be provided in the first imaging device 13A, and a filter that cuts fluorescent light may be provided in the second imaging device 13B.

Figure 3:
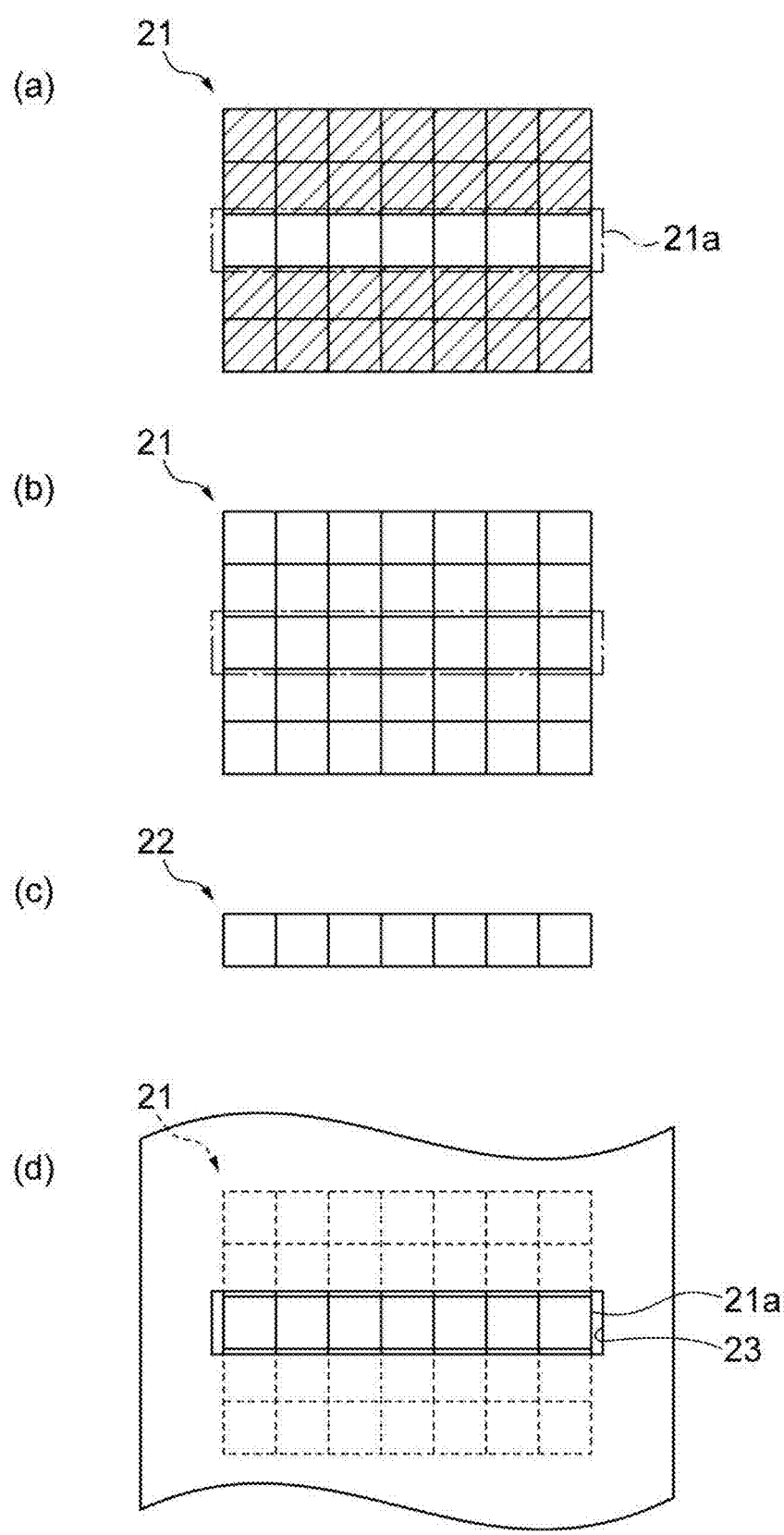
FIG. 3 is a diagram illustrating a configuration example of an imaging unit.

A line scan scheme may be applied to the first imaging device 13A and the second imaging device 13B to partially capture the fluorescent light image and the scattered light image on the irradiation surface R. For example, as illustrated in FIG. 3(a), a subarray may be set on the imaging surface of the area image sensor 21. In this case, since only a pixel row 21a included in the subarray can be read, the light image of the observation light L3 can be partially captured. Further, all pixel rows of the area image sensor 21 may be used as a readout area, and a part of the two-dimensional image may be extracted through a subsequent image process, as illustrated in FIG. 3(b).

Further, partial imaging may be performed by using a line sensor 22 instead of the area image sensor 21 and limiting the imaging surface itself to one pixel row, as illustrated in FIG. 3(c). As illustrated in FIG. 3(d), a slit 23 that transmits only a part of the observation light L3 may be disposed on a front surface of the area image sensor 21, and image data of the pixel row 21a corresponding to the slit 23 may be acquired. When the slit 23 is used, a point sensor of a photomultiplier tube or the like may be used instead of the area image sensor.

The computer 14 physically includes a memory such as a RAM and a ROM, a processor (an arithmetic circuit) such as a CPU, a communication interface, a storage unit such as a hard disk, and a display unit such as a display. Examples of such a computer 14 include a personal computer, a microcomputer, a cloud server, and a smart device (a smart phone, a tablet terminal, or the like). The computer 14 functions as a controller that controls operations of the light source 15, the scanning unit 12, and the imaging unit 13 by a program stored in the memory being executed by a CPU of a computer system.

The computer 14 as the controller receives an input of a measurement start operation from the user, and drives the light source 15, the scanning unit 12, and the imaging unit 13 in synchronization. Accordingly, the sample container 2 is scanned in the Y direction with respect to the irradiation surface R, and a plurality of XZ images in the irradiation surface R are captured by the imaging unit 13. The computer 14 may control the light source 15 so that the light source 15 continuously outputs the light L1 during movement of the sample container 2 by the scanning unit 12, or may control ON/OFF of the output of the light L1 from the light source 15 according to the imaging in the imaging unit 13. Further, when the irradiation optical system 11 includes an optical shutter, the computer 14 may turn ON/OFF the irradiation with the planar light L2 by controlling the optical shutter.

Figure 4:
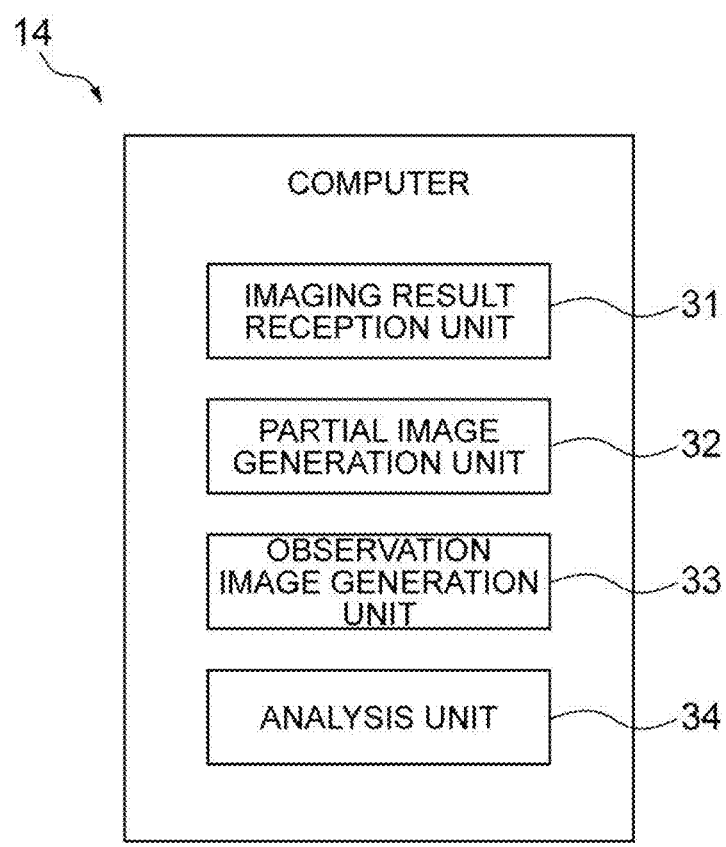
FIG. 4 is a block diagram illustrating an example of functional components of a computer constituting the sample observation device.

Further, as illustrated in FIG. 4, the computer 14 includes an imaging result reception unit 31, a partial image generation unit 32, an observation image generation unit 33, and an analysis unit 34 as functional components. The imaging result reception unit 31 is a unit that receives imaging data from the imaging unit 13. That is, the imaging result reception unit 31 receives fluorescent light image data based on the fluorescent light image included in the observation light L3 from the first imaging device 13A, and receives scattered light image data based on the scattered light image included in the observation light L3 from the second imaging device 13B. The imaging result reception unit 31 outputs the received fluorescent light image data and the received scattered light image data to the partial image generation unit 32.

Figure 5:
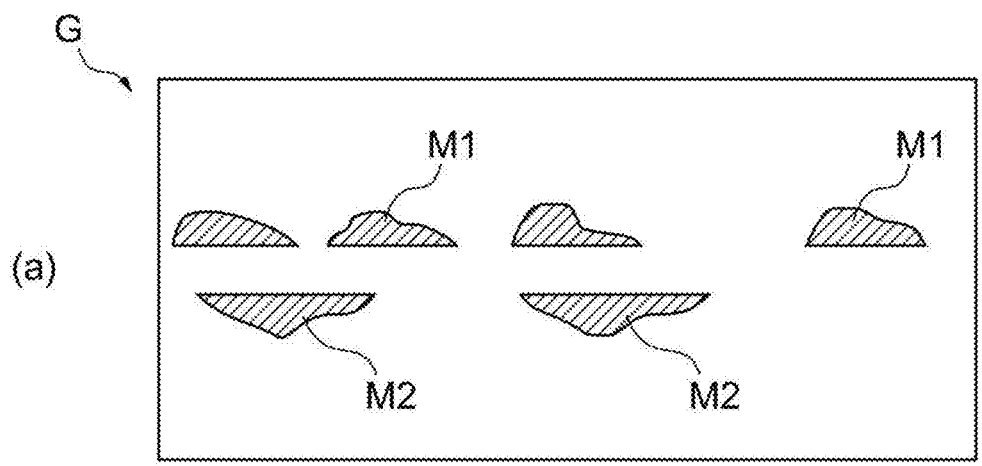
FIG. 5($a$) is a diagram illustrating an example of fluorescent light image data, 5($b$) is a diagram illustrating an example of scattered light image data, and 5($c$) is a diagram illustrating a specific state of a first area and a second area.
Figure 5:
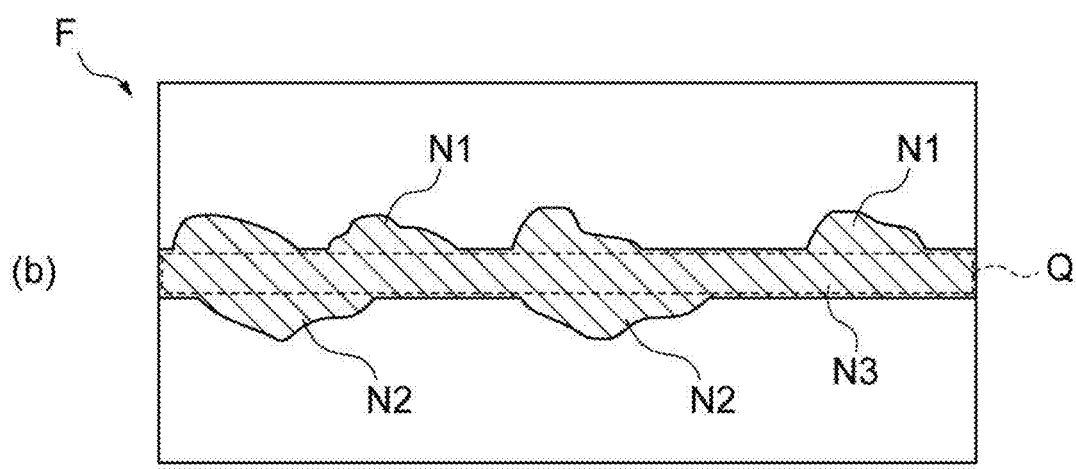
Figure 5:
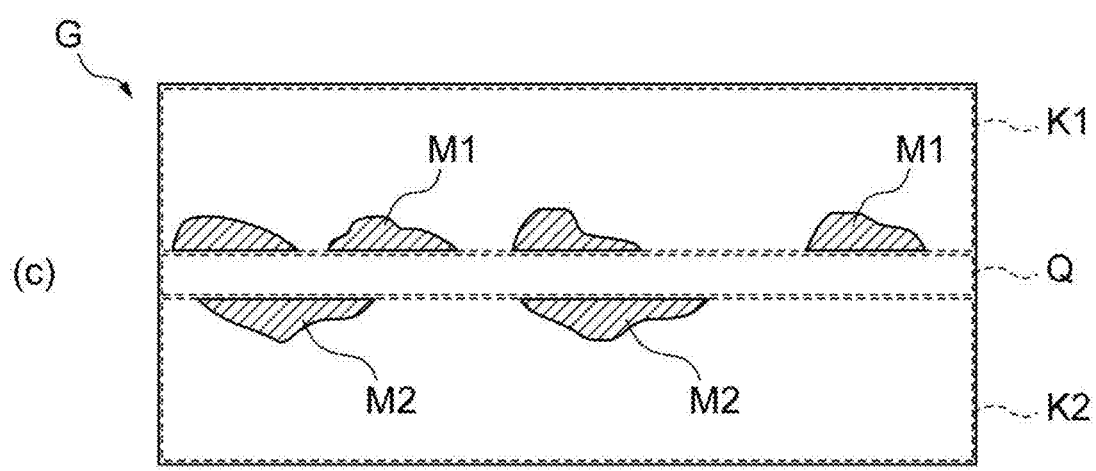

FIG. 5(a) is a diagram illustrating an example of the fluorescent light image data. This fluorescent light image data G corresponds to an XZ image of the fluorescent light generated on the irradiation surface R for the planar light L2. The fluorescent light is generated when the fluorescent substance included in the sample S is excited by the planar light L2. Therefore, as illustrated in FIG. 5(a), a fluorescent light image M1 corresponding to the sample S located on the one surface of the membrane filter 6 and a fluorescent light image M2 corresponding to the sample S located on the other surface of the membrane filter 6 can appear in the fluorescent light image data G. Since the membrane filter 6 does not generate fluorescent light, a fluorescent light image does not appear in an area corresponding to the membrane filter 6.

FIG. 5(b) illustrates an example of the scattered light image data. This scattered light image data F corresponds to an XZ image of the scattered light generated on the irradiation surface R for the planar light L2. The scattered light is generated when the planar light L2 is scattered in the membrane filter 6. Therefore, as illustrated in FIG. 5(b), a scattered light image N1 corresponding to the sample S located on the one surface of the membrane filter 6, a scattered light image N2 corresponding to the sample S located on the other surface of the membrane filter 6, and a scattered light image N3 corresponding to the membrane filter 6 may appear in the scattered light image data F.

The partial image generation unit 32 generates partial image data based on the fluorescent light image data. When the partial image generation unit 32 receives the fluorescent light image data G and the scattered light image data F from the imaging unit 13, the partial image generation unit 32 first specifies an area Q corresponding to the membrane filter 6 (see FIG. 5 (b)) on the basis of the scattered light image N3 in the scattered light image data F. The area Q corresponding to the membrane filter 6 may be specified through predetermined image processing, or may be specified on the basis of the thickness of the membrane filter 6.

Then, as illustrated in FIG. 5(c), the partial image generation unit 32 applies the area Q corresponding to the membrane filter 6 to the fluorescent light image data G, and specifies a first area K1 corresponding to the first sample holding space V1 and a second area K2 corresponding to the second sample holding space V2 in the fluorescent light image data G. After the partial image generation unit 32 specifies the first area K1 and the second area K2, the partial image generation unit 32 extracts a portion corresponding to the first area K1 from the fluorescent light image data G, and generates first partial image data E1 corresponding to the first area K1, as illustrated in FIG. 6(a). Similarly, the partial image generation unit 32 extracts a portion corresponding to the second area K2 from the fluorescent light image data G, and generates second partial image data E2 corresponding to the second area K2, as illustrated in FIG. 6(b). The partial image generation unit 32 outputs the generated first partial image data E1 and the generated second partial image data E2 to the observation image generation unit 33.

The observation image generation unit 33 generates observation image data on the basis of the partial image data. The observation image generation unit 33 compresses the first partial image data E1 and the second partial image data E2 received from the partial image generation unit 32 in a Z-axis direction. The partial image data compressed in the Z-axis direction indicates luminance of the fluorescent light in an X-axis direction. As described above, in the sample observation device 1, the sample container 2 is scanned in a Y-axis direction with respect to the irradiation surface R, and a plurality of XZ images on the irradiation surface R are captured by the imaging unit 13. Therefore, the observation image generation unit 33 generates, for the Y-axis direction, a plurality of pieces of partial image data compressed in the Z-axis direction.

Figure 7:
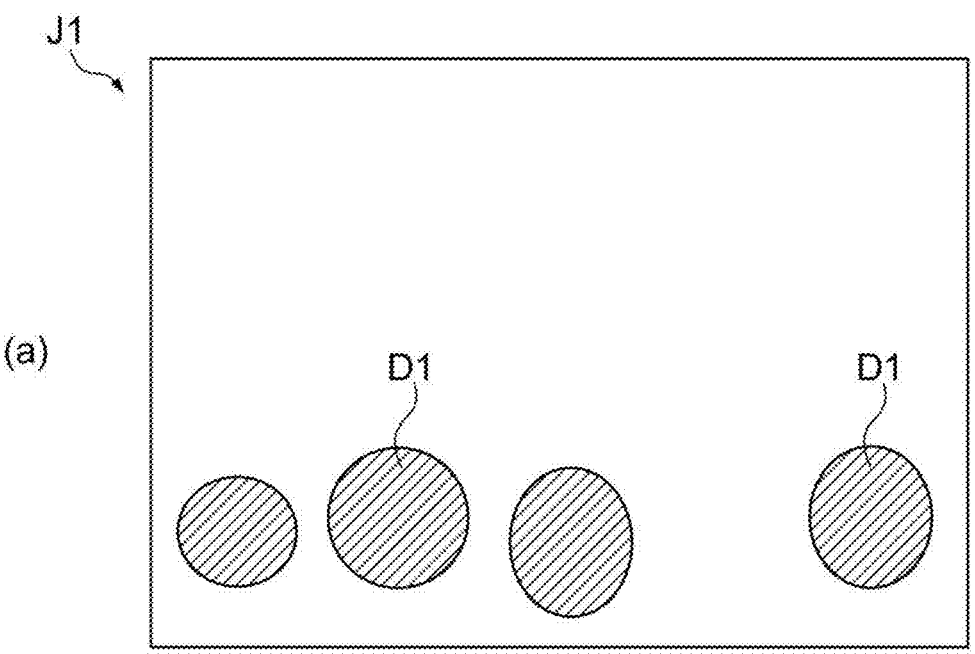
FIG. 7($a$) is a diagram illustrating an example of first observation image data, and 7($b$) is a diagram illustrating an example of second observation image data.
Figure 7:
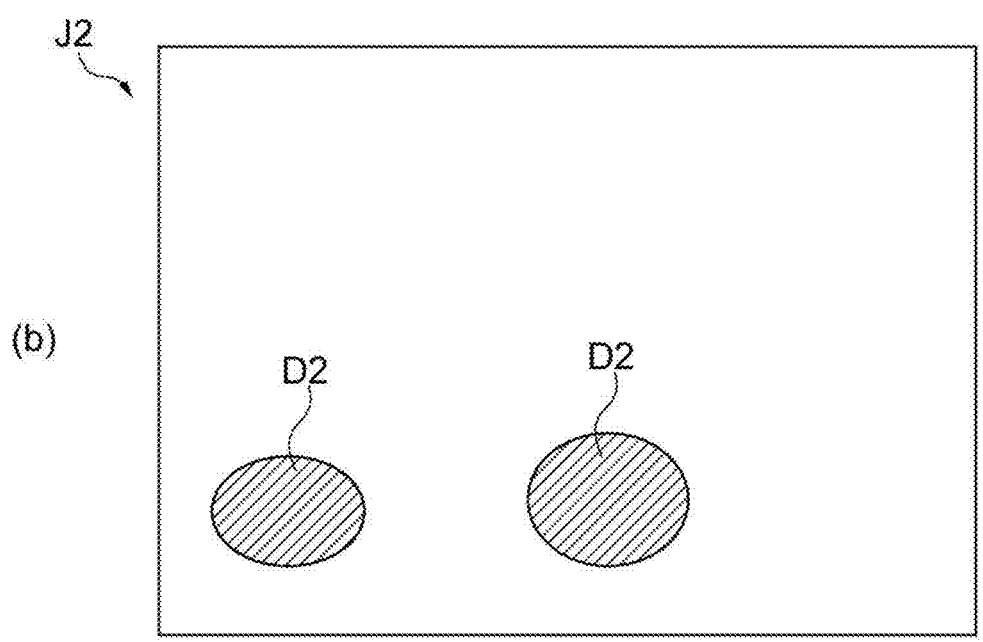

The observation image generation unit 33 synthesizes the partial image data compressed in the Z-axis direction with respect to the first partial image data E1 in the Y-axis direction, and integrates the luminance of the fluorescent light in each of piece of partial image data. Accordingly, as illustrated in FIG. 7(*a*), first observation image data J1 corresponding to the first area K1 is generated. Similarly, the observation image generation unit 33 synthesizes the partial image data compressed in the Z-axis direction with respect to the second partial image data E2 in the Y-axis direction, and integrates the luminance of the fluorescent light in each of piece of partial image data. Accordingly, as illustrated in FIG. 7(*b*), second observation image data J2 corresponding to the second area K2 is generated. The observation image generation unit 33 outputs the generated first observation image data J1 and the generated second observation image data J2 to the analysis unit 34.

The analysis unit 34 analyzes the sample S on the basis of the first observation image data J1 and the second observation image data J2. A fluorescent light image D1 appearing in the first observation image data J1 represents the sample S remaining in the first sample holding space V1 instead of passing through the membrane filter 6. Further, the fluorescent light image D2 appearing in the second observation image data represents the sample S that has passed through the membrane filter 6 and moved to the second sample holding space V2. The analysis unit 34 counts the number of samples S located in the first sample holding space V1 by counting the fluorescent light images D1 appearing in the first observation image data J1. Further, the analysis unit 34 counts the number of samples S located in the second sample holding space V2 by counting the fluorescent light images D2 appearing in the second observation image data J2. The analysis unit 34 may analyze an intensity of the fluorescent light of each of the sample S located in the first sample holding space V1 and the sample S located in the second sample holding space V2 on the basis of intensities of the fluorescent light of the fluorescent light images D1 and D2.

Figure 8:
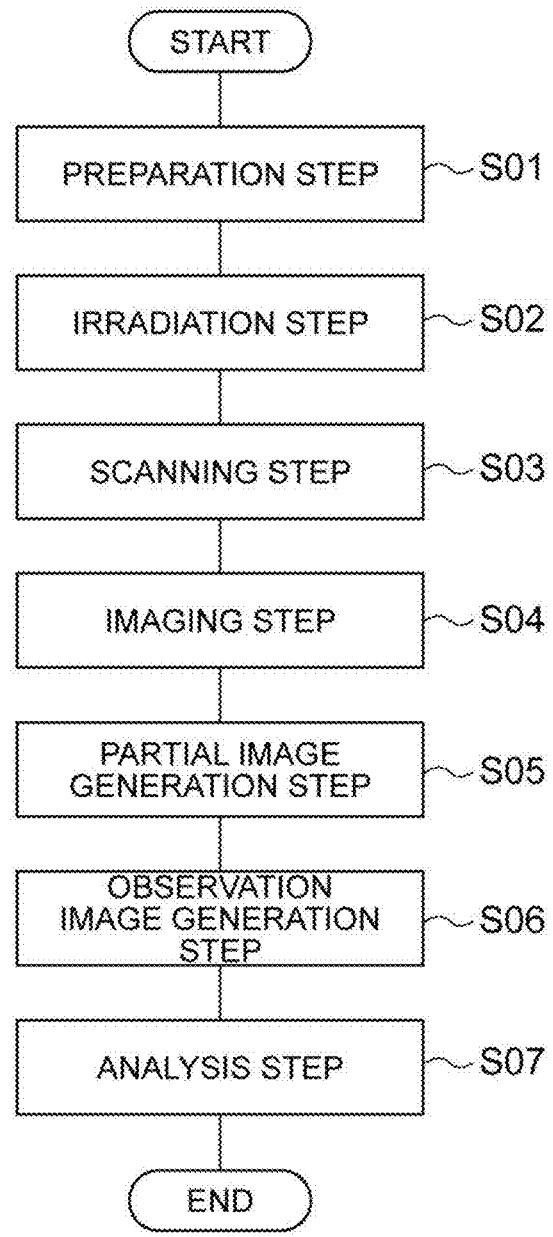

Next, a sample observation method using the sample observation device 1 described above will be described. FIG. 8 is a flowchart illustrating an example of a sample observation method using the sample observation device 1 illustrated in FIG. 1.

As illustrated in FIG. 8, this sample observation method includes a preparation step (step S01), an irradiation step (step S02), a scanning step (step S03), an imaging step (step S04), a partial image generation step (step S05), an observation image generation step (Step S06), and an analysis step (step S07).

In the preparation step, the sample S is held in the sample container 2. Here, the sample S is stained with a fluorescent substance excited by light having a wavelength that is transmitted through the membrane filter 6. Then, the sample S is held on the one surface of the membrane filter 6 coated with the extracellular matrix so that the sample S is located on the first sample holding space V1 side. After a certain time has elapsed after the sample S is held, the sample container 2 is set in the scanning unit 12.

In the irradiation step, the sample S is irradiated with the planar light L2. When a measurement start operation is input to the sample observation device 1 by the user, the light source 15 is driven on the basis of a control signal from the computer 14, and the light L1 is output from the light source 15. The light L1 output from the light source 15 is shaped by the planar light formation unit 16 to become the planar light L2, and the sample S held in the sample container 2 is irradiated with the planar light L2.

In the scanning step, the sample S is scanned with respect to the irradiation surface R for the planar light L2. When the measurement start operation is input by the user, the scanning unit 12 is driven in synchronization with the driving of the light source 15 on the basis of a control signal from the computer 14. Accordingly, the sample container 2 is linearly driven at a constant speed in the Y-axis direction, and the sample S in the well 3 is scanned with respect to the irradiation surface R for the planar light L2.

In the imaging step, the observation light L3 generated due to the irradiation with the planar light L2 is imaged. More specifically, in the imaging step, the observation light L3 generated in the sample S due to the irradiation with the planar light L2 is formed as an image on an image formation surface of the imaging unit 13 by the image formation optical system 17 having the observation axis P2 inclined with respect to the irradiation surface R. In the imaging step, a plurality of partial images corresponding to parts of the light image according to the fluorescent light image formed by the image formation optical system 17 are acquired by the first imaging device 13A, and a plurality of partial images corresponding to parts of the light image according to the scattered light image are acquired by the second imaging device 13B.

In the partial image generation step, the first partial image data E1 corresponding to the first area K1 and the second partial image data E2 corresponding to the second area K2 are generated. In the partial image generation step, the area Q (see FIG. 5(*b*)) corresponding to the membrane filter 6 is first specified on the basis of the scattered light image data F. Then, the area Q corresponding to the membrane filter 6 is applied to the fluorescent light image data G, and the first area K1 corresponding to the first sample holding space V1 and the second area K2 corresponding to the second sample holding space V2 are specified in the fluorescent light image data G (see FIG. 5(*c*)).

Figure 6:
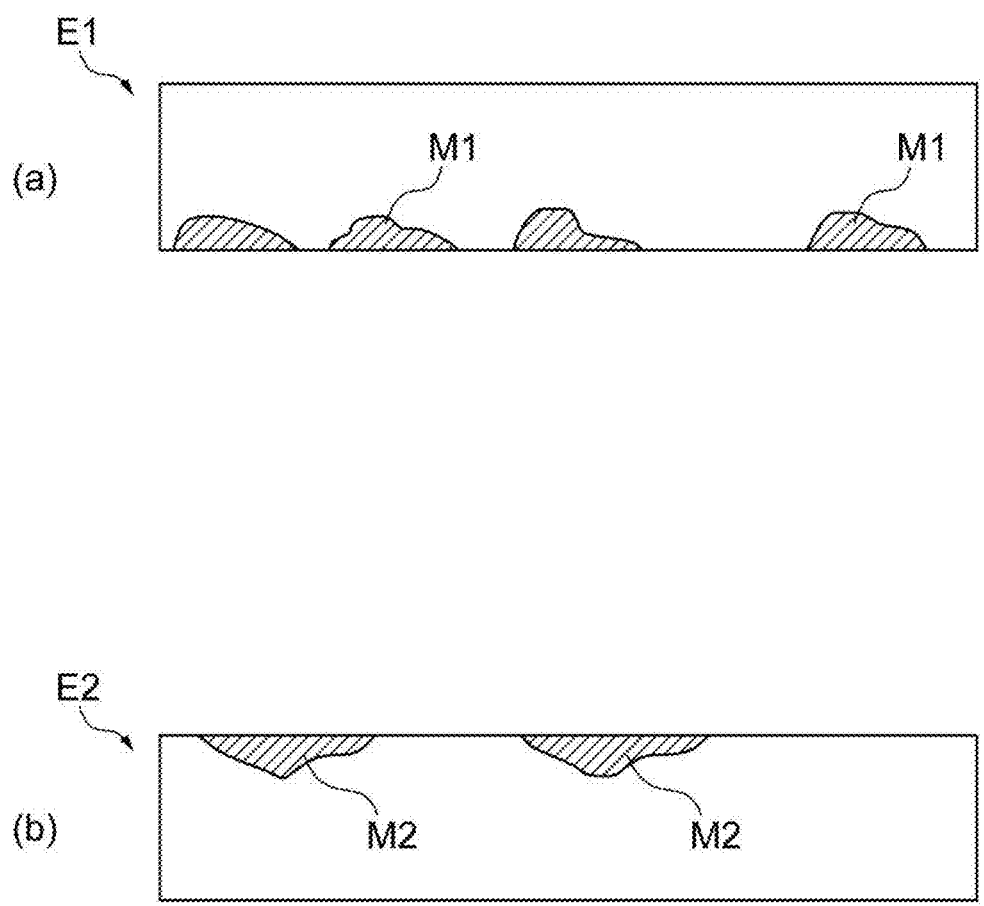
FIG. 6($a$) is a diagram illustrating an example of first partial image data, and 6($b$) is a diagram illustrating an example of second partial image data.

After the first area K1 and the second area K2 are specified, a part corresponding to the first area K1 is extracted from the fluorescent light image data G, and the first partial image data E1 corresponding to the first area K1 is generated (See FIG. 6(*a*)). Similarly, a part corresponding to the second area K2 is extracted from the fluorescent light image data G, and the second partial image data E2 corresponding to the second area K2 is generated (see FIG. 6(*b*)).

In the observation image generation step, the first observation image data J1 is generated on the basis of the first partial image data E1, and the second observation image data J2 is generated on the basis of the second partial image data E2. More specifically, in the observation image generation step, for the first partial image data E1, a plurality of pieces of partial image data compressed in the Z-axis direction is synthesized in the Y-axis direction, and the first observation image data J1 corresponding to the first area K1 is generated (see FIG. 7(*a*)). Similarly, for the second partial image data E2, a plurality of pieces of partial image data compressed in the Z-axis direction is synthesized in the Y-axis direction, the second observation image data J2 corresponding to the second area K2 is generated. (see FIG. 7(b)).

In the analysis step, the sample S is analyzed on the basis of the first observation image data J1 and the second observation image data J2. In the analysis step, for example, the number of samples S located in the first sample holding space V1 is counted by counting the fluorescent light images D1 appearing in the first observation image data J1. Further, the number of samples S located in the second sample holding space V2 is counted by counting the fluorescent light images D2 appearing in the second observation image data J2. An intensity of the fluorescent light of each of the sample S located in the first sample holding space V1 and the sample S located in the second sample holding space V2 is analyzed.

As described above, in the sample observation device 1, the sample is irradiated with the planar light L2 including the wavelength that is transmitted through the membrane filter 6 as excitation light. Accordingly, the fluorescent light image data G based on the imaging result of the observation light L3 including the fluorescent light from both the first sample holding space V1 and the second sample holding space V2 partitioned by the membrane filter 6 can be acquired. Further, in the sample observation device 1, the first area K1 corresponding to the first sample holding space V1 and the second area K2 corresponding to the second sample holding space V2 are specified from the acquired fluorescent light image data G, and the observation image data based on the partial image data of each area is generated. Accordingly, both the sample S that has moved through the membrane filter 6 and the sample S that has not moved can be observed.

Further, in the sample observation device 1, the imaging unit 13 includes the first imaging device 13A that images fluorescent light and the second imaging device 13B that images scattered light. The partial image generation unit 32 specifies the first area K1 and the second area K2 in the fluorescent light image data on the basis of the scattered light image data. Accordingly, the area Q corresponding to the membrane filter 6 in the fluorescent light image data G can be specified using the scattered light image data F. Therefore, the first area K1 and the second area K2 in the fluorescent light image data G can be easily specified.

Further, in the sample observation device 1, the analysis unit 34 counts the number of samples S located in the first sample holding space V1 and the number of samples S located in the second sample holding space V2 on the basis of the first observation image data J1 and the second observation image data J2. Accordingly, the evaluation of the sample S can be performed rapidly.

Further, in the sample observation device 1, an image formation optical system 17 that has an observation axis P2 that is inclined with respect to the irradiation surface R3 and that forms the observation light L3 as an image on the imaging unit 13 is provided. In this case, a field-of-view selection operation becomes unnecessary, and scanning and imaging of the sample S can be performed simultaneously. Therefore, improvement of a throughput until the observation image data is obtained can be achieved.

Figure 9:
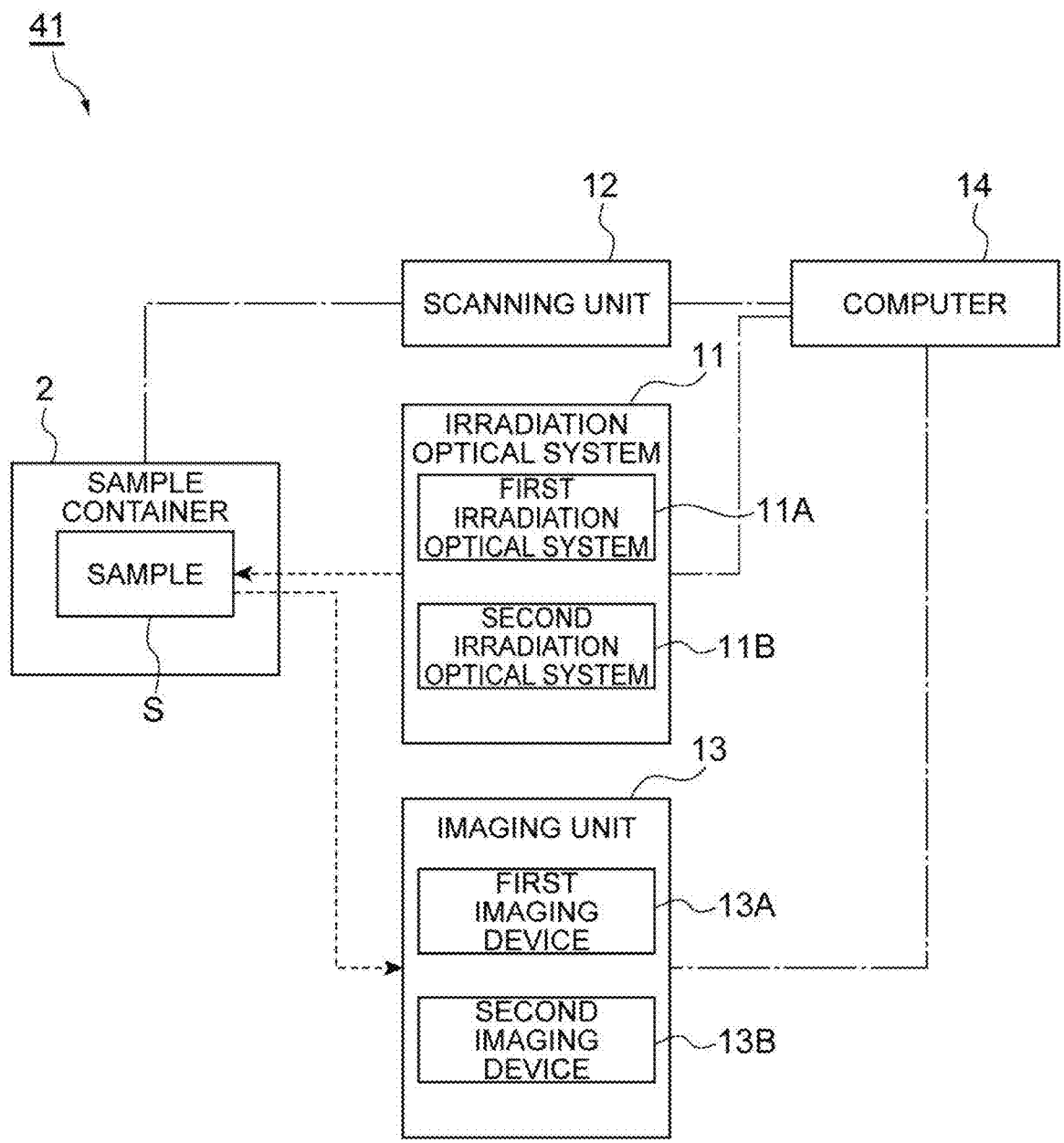
FIG. 9 is a block diagram illustrating another form of the sample observation device.

FIG. 9 is a block diagram illustrating another embodiment of the sample observation device. As illustrated in FIG. 9, a sample observation device 41 according to another embodiment is different from the above-described sample observation device 1 in that the irradiation optical system 11 includes a first irradiation optical system 11A and a second irradiation optical system 11B.

When a sample S is observed using this sample observation device 41, the sample S is stained by a first fluorescent substance excited by light having a wavelength that is transmitted through a membrane filter 6 and a second fluorescent substance excited by light having a wavelength that is not transmitted through the membrane filter 6. Examples of the first fluorescent substance include calcein AM (excitation wavelength 490 nm/fluorescent light wavelength 525 nm). Further, examples of the second fluorescent substance include calcein blue (excitation wavelength 360 nm/fluorescent light wavelength 450 nm).

Figure 10:
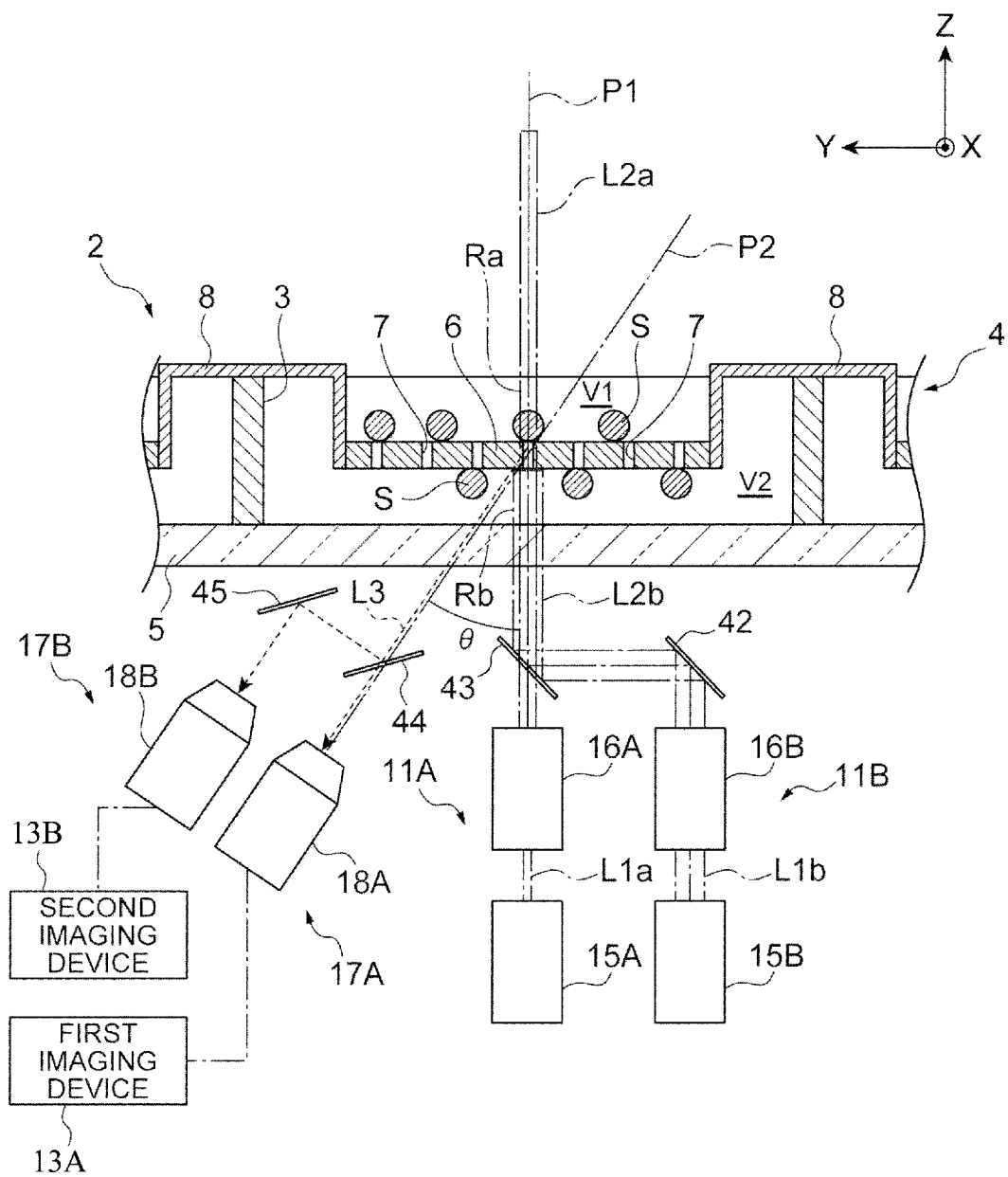
FIG. 10 is a schematic diagram illustrating a configuration example of an irradiation optical system, a sample container, and an image formation optical system in the sample observation device illustrated in FIG. 9.

As illustrated in FIG. 10, the first irradiation optical system 11A includes a first light source 15A and a first planar light formation unit 16A. The first light source 15A outputs first light L1a that is transmitted through the membrane filter 6 and that includes a wavelength that excites the first fluorescent substance. The first planar light formation unit 16A shapes the first light L1a output from the first light source 15A into first planar light L2a, and irradiates the sample S with the first planar light L2a along an optical axis P1. Since the first planar light L2a is transmitted through the membrane filter 6, an irradiation surface Ra for the first planar light L2a reaches a second sample holding space V2 through the membrane filter 6 from a first sample holding space V1.

The second irradiation optical system 11B includes a second light source 15B and a second planar light formation unit 16B. The second light source 15B outputs second light L1b that is not transmitted through the membrane filter 6 and that includes a wavelength that excites the second fluorescent substance. The second planar light formation unit 16B shapes the second light Lib output from the second light source 15B into second planar light L2b, and irradiates the sample S with the second planar light L2b, for example, in a state in which the second planar light L2b is caused to be coaxial with the optical axis P1 by a mirror 42 and a dichroic mirror 43. Since the second planar light L2b is not transmitted through the membrane filter 6, an irradiation surface Rb for the second planar light L2b is present only in the second sample holding space V2.

In the embodiment, the observation light L3 includes the first fluorescent light excited in the sample S by the first planar light L2a and the second fluorescent light excited in the sample S by the second planar light L2b. The first fluorescent light is formed as an image on an imaging surface of the first imaging device 13A by the image formation optical system 17A having the observation axis P2 inclined with respect to the irradiation surface Ra, and the second fluorescent light is split from the first fluorescent light by, for example, a dichroic mirror 44 and a mirror 45 and formed as an image on an image formation surface of the second imaging device 13B by the image formation optical system 17B having the observation axis P2 inclined with respect to the irradiation surface Rb.

The first imaging device 13A captures a first fluorescent light image generated due to the irradiation with the first planar light L2a, and outputs the first fluorescent light image data to the computer 14. The second imaging device 13B captures a second fluorescence light image generated due to the irradiation with the second planar light L2b and outputs the second fluorescent light image data to the computer 14. A filter that cuts the second fluorescent light may be provided in the first imaging device 13A, and a filter that cuts the first fluorescent light may be provided in the second imaging device 13B.

Figure 11:
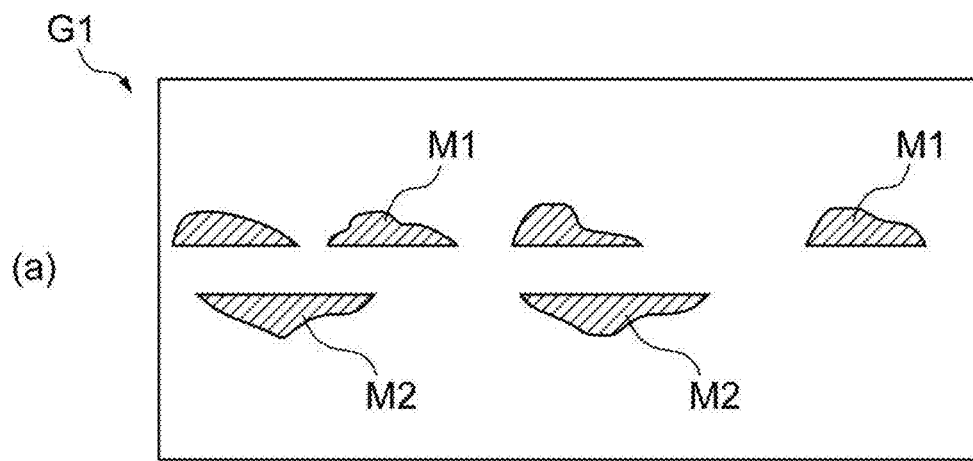
FIG. 11($a$) is a diagram illustrating an example of first fluorescent light image data, FIG. 11($b$) is a diagram illustrating an example of second fluorescent light image data, and FIG. 11($c$) is a diagram illustrating a specific state of the first area and the second area.
Figure 11:
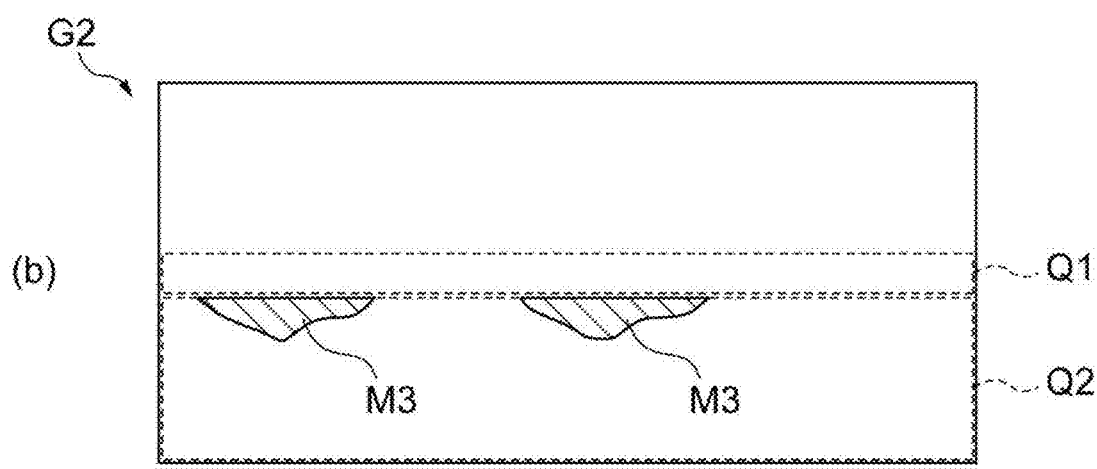
Figure 11:
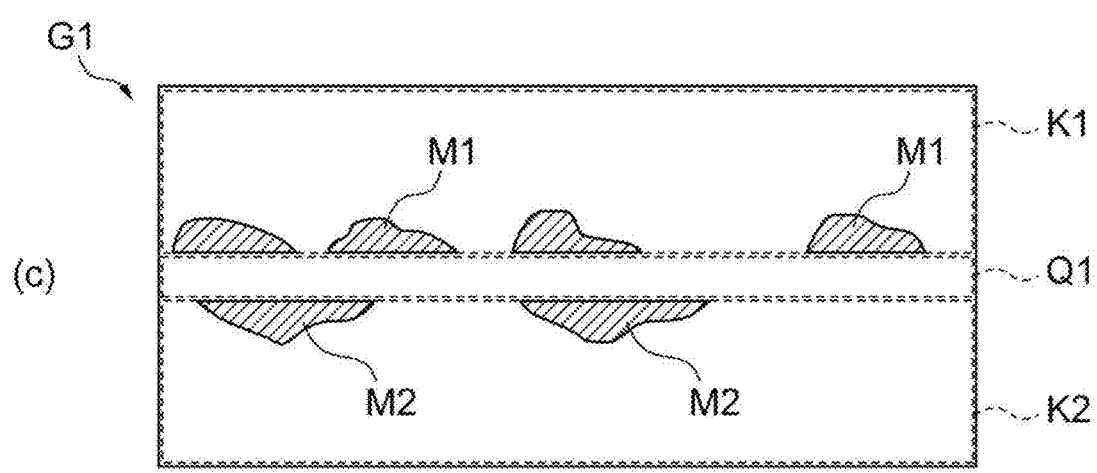

FIG. 11(a) is a diagram illustrating an example of the first fluorescent light image data. The irradiation surface Ra for the first planar light L2a reaches the second sample holding space V2 through the membrane filter 6 from the first sample holding space V1. Therefore, a fluorescent light image M1 corresponding to the sample S located on one surface of the membrane filter 6 and a fluorescent light image M2 corresponding to the sample S located on the other surface of the membrane filter 6 can appear in the first fluorescent light image data G1. Further, FIG. 11(b) is a diagram illustrating an example of the second fluorescent light image data. The irradiation surface Rb for the second planar light L2b is present only in the second sample holding space V2. Therefore, only a fluorescent light image M3 corresponding to the sample S located on the other surface of the membrane filter 6 can appear in the second fluorescent light image data G2.

In this case, the partial image generation unit 32 extracts an area Q1 corresponding to the membrane filter 6 on the basis of a thickness of the membrane filter 6, and extracts an area Q2 corresponding to the second sample holding spaces V2 from the second fluorescent light image data G2 on the basis of a range in which the fluorescent light image M3 appears. As illustrated in FIG. 11(c), the partial image generation unit 32 applies the area Q1 corresponding to the membrane filter 6 and the area Q2 corresponding to the second sample holding space V2 to the first fluorescent light image data G1, and specifies the first area K1 corresponding to the first sample holding space V1 and the second area K2 corresponding to the second sample holding space V2 in the first fluorescent light image data G1.

In such a sample observation device 41, the same operation and effects as in the sample observation device 1 described above can be obtained, and both the sample S that has moved through the membrane filter 6 and the sample S that has not moved can be observed. Further, in the sample observation device 1, an area corresponding to the sample holding space V1 and an area corresponding to the second sample holding space V2 can be easily discriminated on the basis of the fluorescent light images M1 and M2 of the sample S included in the first fluorescent light image data G1 and the fluorescent light image M3 of the sample included in the second fluorescent light image data G2. Therefore, the first area K1 and the second area K2 in the first fluorescent light image data G1 can be easily specified through collation of the first fluorescent light image data G1 with the second fluorescent light image data G2.

Further, it is assumed that it may be difficult to simultaneously stain the sample S with two fluorescent substances according to a type of the sample S. In this case, the sample S is stained with the first fluorescent substance excited by the light having a wavelength that is transmitted through the membrane filter 6, and the solution including the second fluorescent substance excited by the light having a wavelength that is not transmitted through the membrane filter 6 may be injected into the first sample holding space V1 and the second sample holding space V2.

Figure 12:
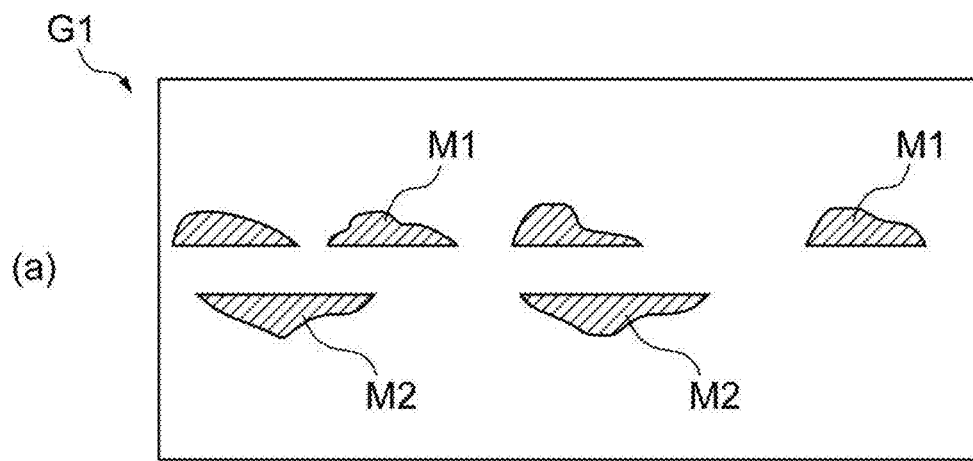
FIG. 12($a$) is a diagram illustrating another example of the first fluorescent light image data, FIG. 12($b$) is a diagram illustrating another example of the second fluorescent light image data, and FIG. 12($c$) is a specific state of the first area and the second area.
Figure 12:
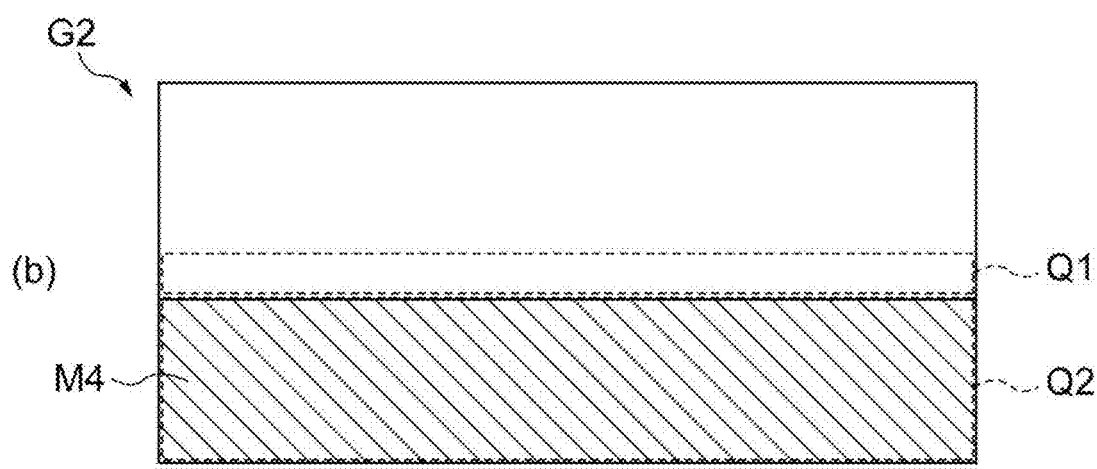
Figure 12:
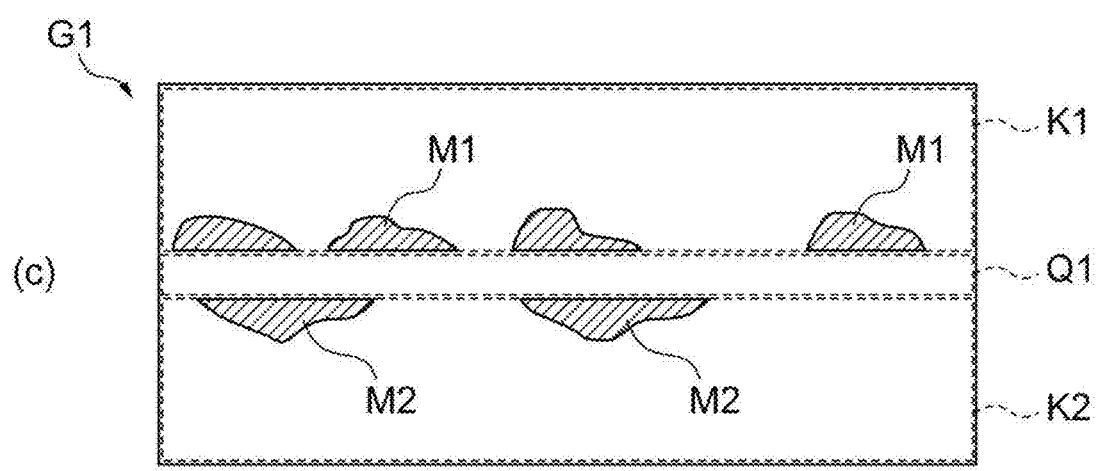

In this case, as illustrated in FIG. 12(a), the fluorescent light image M1 corresponding to the sample S located on the one surface of the membrane filter 6 and the fluorescent light image M2 corresponding to the sample S located on the other surface of the membrane filter 6 can appear in the first fluorescent light image data G1. Further, as illustrated in FIG. 12(b), in the second fluorescent light image data G2, a fluorescent light image corresponding to the sample S does not appear, and only a fluorescent light image M4 corresponding to the solution in the second sample holding space V2 can appear.

In this case, the partial image generation unit 32 extracts the area Q1 corresponding to the membrane filter 6 on the basis of a thickness of the membrane filter 6, and extracts the area Q2 corresponding to the second sample holding spaces V2 from the second fluorescent light image data G2 on the basis of a range in which the fluorescent light image M4 appears. As illustrated in FIG. 12(c), the partial image generation unit 32 applies the area Q1 corresponding to the membrane filter 6 and the area Q2 corresponding to the second sample holding space V2 to the first fluorescent light image data G1, and specifies the first area K1 corresponding to the first sample holding space V1 and the second area K2 corresponding to the second sample holding space V2 in the first fluorescent light image data G1.

In this case, the same operation and effects as in the sample observation device 1 described above can be obtained, and both the sample S that has moved through the membrane filter 6 and the sample S that has not moved can be observed. Further, the area corresponding to the first sample holding space V1 and the area corresponding to the second sample holding space V2 can be easily discriminated on the basis of the fluorescent light image M4 of the solution. Therefore, the first area K1 and the second area K2 in the first fluorescent light image data G1 can be more easily specified through collation of the first fluorescent light image data G1 with the second fluorescent light image data G2.

The present disclosure is not limited to the above embodiment. Further, although the irradiation optical system 11 that outputs the planar light and the imaging unit 13 that adopts the line scan scheme are combined, for example, in the above-described embodiment, another scheme may be adopted as long as a cross section in a depth direction of the well 3 in the sample container 2 can be measured at a time. For example, an optical system of oblique plane microscopy described in U.S. Pat. No. 8,582,203 may be adopted.

REFERENCE SIGNS LIST 1,41: Sample observation device
2: Sample container
6: Membrane filter
11, 11A, 11B: Irradiation optical system
12: Scanning unit
13: Imaging unit
17, 17A, 17B: Image formation optical system
32: Partial image generation unit
33: Observation image generation unit
34: Analysis unit
E1: First partial image data
E2: Second partial image data
F: Scattered light image data
G: Fluorescent image data
G1: First fluorescent light image data
G2: Second fluorescent light image data
J1: First observation image data
J2: Second observation image data
K1: First area
K2: Second area
L2: Planar light
L2a: First planar light
L2b: Second planar light
L3: Observation light
R, Ra, Rb: Irradiation surface
S: Sample
V1: First sample holding space
V2: Second sample holding space

The invention claimed is:

1. A device for observing a sample held in a sample container having a first sample holding space and a second sample holding space partitioned by a membrane filter, the device comprising:
   an irradiation optical system configured to irradiate the sample with planar light including a wavelength that is transmitted through the membrane filter as excitation light;
   a scanner configured to scan the sample with respect to an irradiation surface for the planar light;
   an imaging unit configured to image observation light including fluorescent light generated due to the irradiation with the planar light and outputs fluorescent light image data based on an imaging result;
   a partial image generator configured to specify a first area corresponding to the first sample holding space and a second area corresponding to the second sample holding space in the fluorescent light image data, and generates first partial image data corresponding to the first area and second partial image data corresponding to the second area;
   an observation image generator configured to generate first observation image data on the basis of the first partial image data and generates second observation image data on the basis of the second partial image data; and
   an analyzer configured to analyze the sample on the basis of the first observation image data and the second observation image data.

2. The device according to claim 1,
   wherein the imaging unit further images scattered light of the excitation light generated due to the irradiation with the planar light, and outputs scattered light image data based on an imaging result, and
   the partial image generator specifies the first area and the second area in the fluorescent light image data on the basis of the scattered light image data.

3. The device according to claim 1,
   wherein the irradiation optical system irradiates the sample with first planar light including a wavelength that is transmitted through the membrane filter and second planar light including a wavelength that is not transmitted through the membrane filter as the excitation light,
   the imaging unit images observation light including first fluorescent light generated due to irradiation with the first planar light and observation light including second fluorescent light generated due to irradiation with the second planar light, and outputs first fluorescent light image data and second fluorescent light image data based on respective imaging results, and
   the partial image generator specifies the first area and the second area in the first fluorescent light image data on the basis of the second fluorescent light image data.

4. The device according to claim 3,
   wherein the sample is stained with a first fluorescent substance excited by light having a wavelength that is transmitted through the membrane filter, and a second fluorescent substance excited by light having a wavelength that is not transmitted through the membrane filter.

5. The device according to claim 3,
   wherein the sample is stained with a first fluorescent substance excited by light having a wavelength that is transmitted through the membrane filter, and a solution including a second fluorescent substance excited by light having a wavelength that is not transmitted through the membrane filter is injected into the first sample holding space and the second sample holding space.

6. The device according to claim 1,
   wherein the analyzer counts the number of samples located in the first sample holding space and the number of samples located in the second sample holding space on the basis of the first observation image data and the second observation image data.

7. The device according to claim 1, further comprising:
   an image formation optical system that has an observation axis inclined with respect to the irradiation surface and configured to form an image of the observation light on the imaging unit.

8. A method for observing a sample held in a sample container having a first sample holding space and a second sample holding space partitioned by a membrane filter, the method comprising:
   irradiating the sample with planar light including a wavelength that is transmitted through the membrane filter as excitation light;
   scanning the sample with respect to an irradiation surface for the planar light;
   imaging observation light including fluorescent light generated due to the irradiation with the planar light and outputting fluorescent light image data based on an imaging result;
   specifying a first area corresponding to the first sample holding space and a second area corresponding to the second sample holding space in the fluorescent light image data, and generating first partial image data corresponding to the first area and second partial image data corresponding to the second area;
   generating first observation image data on the basis of the first partial image data and generating second observation image data on the basis of the second partial image data; and
   analyzing the sample on the basis of the first observation image data and the second observation image data.

9. The method according to claim 8,
   wherein the imaging includes further imaging scattered light of the excitation light generated due to the irradiation with the planar light, and outputting scattered light image data based on an imaging result, and
   the specifying includes specifying the first area and the second area in the fluorescent light image data on the basis of the scattered light image data.

10. The method according to claim 8,
    wherein the irradiation includes irradiating the sample with first planar light including a wavelength that is transmitted through the membrane filter and second planar light including a wavelength that is not transmitted through the membrane filter as the excitation light,
    the imaging includes imaging observation light including first fluorescent light generated due to irradiation with the first planar light and observation light including second fluorescent light generated due to irradiation with the second planar light, and outputting first fluorescent light image data and second fluorescent light image data based on respective imaging results, and
    the generation includes specifying the first area and the second area in the first fluorescent light image data on the basis of the second fluorescent light image data.

11. The method according to claim 10, further comprising:
staining the sample with a first fluorescent substance excited by light having a wavelength that is transmitted through the membrane filter, and a second fluorescent substance excited by light having a wavelength that is not transmitted through the membrane filter.

12. The method according to claim 10, further comprising:
staining the sample with a first fluorescent substance excited by light having a wavelength that is transmitted through the membrane filter, and injecting a solution including a second fluorescent substance excited by light having a wavelength that is not transmitted through the membrane filter into the first sample holding space and the second sample holding space.

13. The method according to claim 8,
wherein the analyzing includes counting the number of samples located in the first sample holding space and the number of samples located in the second sample holding space on the basis of the first observation image data and the second observation image data.

14. The method according to claim 8, wherein the imaging includes forming an image of the observation light according to an observation axis inclined with respect to the irradiation surface.

* * * * *